United States Patent [19] [11] Patent Number: 4,786,310
Haga et al. [45] Date of Patent: Nov. 22, 1988

[54] BENZOTHIAZOLYLAZOLIDINES, AND THEIR PRODUCTION AND USE

[75] Inventors: Toru Haga, Takarazuka; Eiki Nagano, Nishinomiya; Kouichi Morita; Ryo Sato, both of Toyonaka, all of Japan

[73] Assignee: Sumitomo Chemical Company, Limited, Osaka, Japan

[21] Appl. No.: 750

[22] Filed: Jan. 6, 1987

[30] Foreign Application Priority Data

Jan. 6, 1986 [JP] Japan .................................. 61-1172
Mar. 17, 1986 [JP] Japan .................................. 61-59035

[51] Int. Cl.⁴ .................... C07D 487/04; A01N 43/90
[52] U.S. Cl. ...................................... 71/90; 544/236; 546/121
[58] Field of Search ............... 544/238, 236; 548/264, 548/259, 165; 71/90

[56] References Cited

U.S. PATENT DOCUMENTS 4,452,981 6/1984 Nagano ............................. 548/264
4,578,477 5/1986 D'Amico ............................ 548/165

Primary Examiner—Robert Gerstl
Attorney, Agent, or Firm—Birch, Stewart, Kolasch & Birch

[57] ABSTRACT

A compound of the formula:

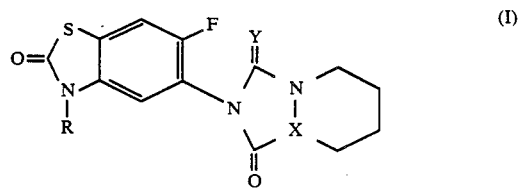

wherein R is a $C_1$-$C_5$ alkyl group, a $C_3$-$C_5$ alkenyl group, a $C_3$-$C_5$ alkynyl group or a $C_1$-$C_3$ alkoxy ($C_1$-$C_3$)alkyl group, X is a nitrogen atom or a methine group and Y is a sulfur atom or an oxygen atom, which is useful as a herbicide.

9 Claims, No Drawings

BENZOTHIAZOLYLAZOLIDINES, AND THEIR PRODUCTION AND USE

The present invention relates to benzothiazolylazolidines, and their production and use. More particularly, the present invention relates to novel benzothiazolylazolidines, a process for producing them, and their use as herbicides.

Some benzothiazolone derivatives (e.g. 4-chloro-2-oxobenzothiazolin-3-ylacetic acid) are known to be effective as herbicides [Herbicide Handbook of the Weed Science Society of America, 5th Ed., p. 40 (1983)]. However, their herbicidal activity is not necessarily satisfactory.

It has now been found that the benzothiazolylazolidines of the formula:

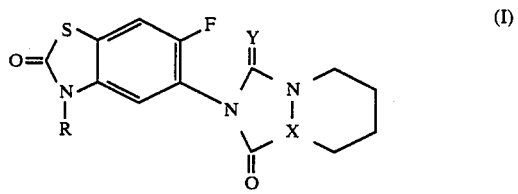

wherein R is a $C_1$–$C_5$ alkyl group, a $C_3$–$C_5$ alkenyl group, a $C_3$–$C_5$ alkynyl group or a $C_1$–$C_3$ alkoxy($C_1$–$C_3$)alkyl, group, X is a nitrogen atom or a methine group (—CH—) and Y is a sulfur atom or an oxygen atom, exhibit a high herbicidal activity against a wide variety of weeds including broad-leaved weeds, Graminaceous weeds, Commelinaceous weeds and Cyperaceous weeds in agricultural plowed fields by foliar or soil treatment without producing any material phytotoxicity on various agricultural crops such as corn, sorghum, wheat, barley, rice plant, soybean, peanut and cotton. Examples of the broad-leaved weeds are wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursa-pastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), tall morningglory (*Ipomoea purpurea*), field bindweed (*Convolvulus arvensis*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), sun spurge (*Euphorbia helioscopia*), etc. Examples of Graminaceous weeds are Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*), etc. Examples of Commelinaceous weeds are asiatic dayflower (*Commelina communis*), etc. Examples of Cyperaceous weeds are rice flatsedge (*Cyperus iria*), etc.

It is also notable that some of the benzothiazolylazolidines (I) exert a prominent herbicidal activity by soil application before or after germination of undesired weeds in the paddy field with no material chemical injury. For instance, they demonstrate a high herbicidal potency on broad-leaved weeds such as common falsepimpernel (*Lindernia procumbens*), indian toothcup (*Rotala indica*), waterwort (*Elatine triandra*), Graminaceous weeds such as barnyardgrass (*Echinochloa oryzicola*), Cyperaceous weeds such as Sm.fl. umbrella sedge (*Cyperus difformis*), hardstem bulrush (*Scirpur juncoides*) and needle spikerush (*Eleocharis acicularis*) and others such as monochoria (*Monochoria vaginalis*) and arrowhead (*Sagittaria pygmaea*) without producing any material phytotoxicity to rice plants on flooding treatment.

Among the benzothiazolylazolidines (I), preferred are those wherein Y is an oxygen atom and R is a $C_2$–$C_4$ alkyl group, a $C_3$–$C_4$ alkenyl group, a $C_3$–$C_4$ alkynyl group or a $C_1$–$C_3$ alkoxymethyl group, particularly an ethyl group, an isopropyl group, an allyl group, a propargyl group, a 1-methyl-2-propynyl group or a methoxymethyl group.

Specific examples of the preferred benzothiazolylazolidines (I) are 2-[3-(2-propynyl)-6-fluoro-2(3H)-benzothiazolon-5-yl]-4,5,6,7-tetrahydroimidazo[1,5-a]pyridine-1,3-(2H,5H)-dione, 2-[3-(2-propynyl)-6-fluoro-2(3H)-benzothiazolon-5-yl]-4,5,6,7-tetrahydro-1H-[1,2,4]triazolo-[1,2-a]pyridazine-1,3(2H)-dione, 2-[3-(2-propynyl)-6-fluoro-2(3H)-benzothiazolon-5-yl]-hexahydro-1-thioxo-1H-[1,2,4]triazolo[1,2-a]pyridazin-3-one, etc.

The benzothiazolylazolidines (I) are obtained by heating a urea compound of the formula:

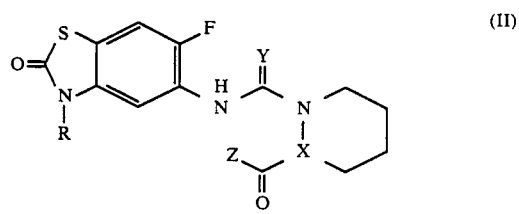

wherein R, X and Y are each as defined above and Z is a $C_1$–$C_3$ alkoxy group in an inert solvent in the presence of a base.

Heating may be carried out at a temperature of 40° to 100° C. for a period of 0.5 to 48 hours. Examples of the solvent are alcohols (e.g. methanol, ethanol, isopropanol, t-butanol), nitriles (e.g. acetonitrile, isobutylonitrile), amides (e.g. formamide, N,N-dimethylformamide), sulfur compounds (e.g. dimethylsulfoxide), and their mixtures. As the base, there may be employed alkali metal alkoxides (e.g. sodium methoxide, sodium ethoxide), fluorine compounds (e.g. sodium fluoride, potassium fluoride), etc. The base is normally used in a catalytic amount to one equivalent per one equivalent of the urea compound (II).

After completion of the reaction, the reaction mixture is subjected to an ordinary post-treatment such as dilution with water, extraction with an organic solvent and concentration. When desired, any conventional purification procedure such as chromatography or recrystallization may be applied.

The benzothiazolylazolidines (I) are also obtainable by reacting an iso(thio)cyanate compound of the formula:

wherein R and Y are each as defined above with an azinoic ester of the formula:

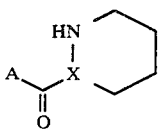

wherein A is a $C_1$-$C_3$ alkoxy group and X is as defined above in an inert solvent in the presence of a base.

The reaction may be carried out at a temperature of 10° to 100° C. for a period of 1 to 40 hours. Examples of the inert solvent are aromatic hydrocarbons (e.g. benzene, toluene, xylene), halogenated hydrocarbons (e.g. chloroform, dichloroethane, chlorobenzene, dichlorobenzene), ethers (e.g. diisopropyl ether, dioxane, ethylene glycol dimethyl ether). Their mixtures are also usable. As the base, there is usually employed an organic base (e.g. triethylamine, diisopropylethylamine, tri-n-butylamine). The amount of the base may be catalytic.

After completion of the reaction, the reaction mixture is subjected to an ordinary post-treatment such as dilution with water, extraction with an organic solvent and concentration. If desired, any conventional purification procedure such as chromatography and recrystallization may be adopted.

Typical examples of the benzothiazolylazolidines (I) which are obtainable through the above procedures are shown in Table 1.

TABLE 1

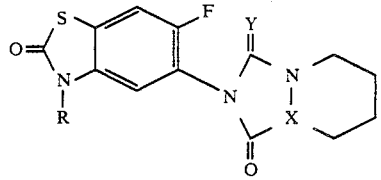

| R | Y | X |
|---|---|---|
| $CH_3$ | O | N |
| $C_2N_5$ | O | N |
| n-$C_3H_7$ | O | N |
| i-$C_3H_7$ | O | N |
| n-$C_4H_9$ | O | N |
| i-$C_4H_9$ | O | N |
| sec-$C_4H_9$ | O | N |
| t-$C_4H_9$ | O | N |
| $CH_2$=$CHCH_2$ | O | N |
| $CH_3CH$=$CHCH_2$ | O | N |
| $CH$≡$CCH_2$ | O | N |
| $CH$≡$C$—$CH$<br>\|<br>$CH_3$ | O | N |
| $CH_3C$≡$CCH_2$ | O | N |
| $CH_3OCH_2$ | O | N |
| $CH_3CH_2OCH_2$ | O | N |
| $CH_3CH_2CH_2OCH_2$ | O | N |
| $CH_3$ | S | N |
| $C_2H_5$ | S | N |
| n-$C_3H_7$ | S | N |
| i-$C_3H_7$ | S | N |
| n-$C_4H_9$ | S | N |
| i-$C_4H_9$ | S | N |
| sec-$C_4H_9$ | S | N |
| t-$C_4H_9$ | S | N |
| $CH_2$=$CHCH_2$ | S | N |
| $CH_3CH$=$CHCH_2$ | S | N |
| $CH$≡$CCH_2$ | S | N |
| $CH$≡$C$—$CH$<br>\|<br>$CH_3$ | S | N |
| $CH_3C$≡$CCH_2$ | S | N |
| $CH_3OCH_2$ | S | N |
| $CH_3CH_2OCH_2$ | S | N |
| $CH_3CH_2CH_2OCH_2$ | S | N |
| $CH_3$ | O | CH |
| $C_2H_5$ | O | CH |
| n-$C_3H_7$ | O | CH |
| i-$C_3H_7$ | O | CH |
| n-$C_4H_9$ | O | CH |
| i-$C_4H_9$ | O | CH |
| sec-$C_4H_9$ | O | CH |
| t-$C_4H_9$ | O | CH |
| $CH_2$=$CHCH_2$ | O | CH |
| $CH_3CH$=$CHCH_2$ | O | CH |
| $CH$≡$CCH_2$ | O | CH |
| $CH$≡$C$—$CH$<br>\|<br>$CH_3$ | O | CH |
| $CH_3C$≡$CCH_2$ | O | CH |
| $CH_3OCH_2$ | O | CH |
| $CH_3CH_2OCH_2$ | O | CH |
| $CH_3CH_2CH_2OCH_2$ | O | CH |
| $CH_3$ | S | CH |
| $C_2H_5$ | S | CH |
| n-$C_3H_7$ | S | CH |
| i-$C_3H_7$ | S | CH |
| n-$C_4H_9$ | S | CH |
| i-$C_4H_9$ | S | CH |
| sec-$C_4H_9$ | S | CH |
| t-$C_4H_9$ | S | CH |
| $CH_2$=$CHCH_2$ | S | CH |
| $CH_3CH$=$CHCH_2$ | S | CH |
| $CH$≡$CCH_2$ | S | CH |
| $CH$≡$C$—$CH$<br>\|<br>$CH_3$ | S | CH |
| $CH_3C$≡$CCH_2$ | S | CH |
| $CH_3OCH_2$ | S | CH |
| $CH_3CH_2OCH_2$ | S | CH |
| $CH_3CH_2CH_2OCH_2$ | S | CH |

Practical and presently preferred embodiments for production of the benzothiazolylazolidines (I) are illustratively shown in the following Examples.

EXAMPLE 1

Ethyl 2-[6-fluoro-3-(2-propenyl)-2(3H)-benzothiazolon-5-ylaminocarbonyl]-hexahydropyridazine-1-carboxylate (1.55 g) was added to a methanolic solution (2.05 g) of 10% sodium methoxide, and the resultant mixture was heated under reflux for 1.5 hours and allowed to cool. Water was added thereto, and the mixture was extracted with ethyl acetate. The extract was washed with water, dried, concentrated and purified by silica gel thin layer chromatography with a mixture of ethyl acetate and hexane (1:1) as an eluent to give 2-[3-(2-propenyl)-6-fluoro-2(3H)-benzothiazolon-5-yl]-hexahydro-1H-[1,2,4]triazolo[1,2-a]pyridazine-1,3-dione (0.15 g). m.p., 199.5° C.

EXAMPLE 2

Ethyl 2-[6-fluoro-3-(2-propenyl)-2(3H)-benzothiazolon-5-ylaminothiocarbonyl]hexahydropyridazine-1-carboxylate (2.61 g) was added to a methanolic solution (2.97 g) of 10% sodium methoxide, and the resultant mixture was heated under reflux for 1.5 hours and allowed to cool. Water was added thereto, and the mixture was extracted with ethyl acetate. The extract was washed with water, dried, concentrated and purified by silica gel thin layer chromatography with a mixture of ethyl acetate and toluene (1:9) as an eluent to give 2-[3-(2-propenyl)-6-fluoro-2(3H)-benzothiazolon-5-yl]-hexahydro-3-thioxo-1H-[1,2,4]triazolo[1,2-a]pyridazin-1-one (0.31 g). m.p., 179°–181° C.

EXAMPLE 3

3-Ethyl-6-fluoro-2(3H)-benzothiazolon-5-yl isocyanate (1.16 g) and ethyl pipecolic acid (1.07 g) were dissolved in toluene (5 ml). A catalytic amount of triethylamine was added thereto, and the resultant mixture was stirred at 25° C. for 12 hours. Water was added to the reaction mixture, which was then extracted with toluene. The extract was dried and concentrated to give 2-[3-ethyl-6-fluoro-2(3H)-benzothiazolon-5-yl]tetrahydroimidazo[1,5-a]-pyridine-1,3(2H,5H)-dione (0.89 g). m.p., 162°–164° C.

In the same manner as above, the benzothiazolylazolidines (I) as shown in Table 2 were obtained.

TABLE 2

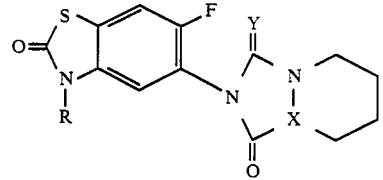

| Compound No. | R | Y | X | Physical property |
|---|---|---|---|---|
| 1 | $CH_3$ | O | N | m.p. 250–251° C. |
| 2 | $C_2H_5$ | O | N | m.p. 194.0–195.0° C. |
| 3 | $n-C_3H_7$ | O | N | m.p. 195.8° C. |
| 4 | $CH_2=CHCH_2$ | O | N | m.p. 199.5° C. |
| 5 | $CH\equiv CCH_2$ | O | N | m.p. 61.7° C. |
| 6 | $CH_3OCH_2$ | O | N | m.p. 186–188° C. |
| 7 | $CH_3CH_2OCH_2$ | O | N | m.p. 197–198° C. |
| 8 | $C_2H_5$ | S | N | m.p. 116–117° C. |
| 9 | $n-C_3H_7$ | S | N | m.p. 182.5–183.5° C. |
| 10 | $CH_2=CHCH_2$ | S | N | m.p, 179–181° C. |
| 11 | $CH\equiv CCH_2$ | S | N | m.p. 36–38° C. |
| 12 | $CH_3$ | O | CH | m.p. 156.4° C. |
| 13 | $C_2H_5$ | O | CH | m.p. 162–164° C. |
| 14 | $n-C_3H_7$ | O | CH | m.p. 88.9° C. |
| 15 | $CH_2=CHCH_2-$ | O | CH | m.p, 36.5–38° C. |
| 16 | $CH\equiv CCH_2-$ | O | CH | m.p. 156–158° C. |
| 17 | $CH_3OCH_2-$ | O | CH | $n_D^{26.2}$ 1.5722 |
| 18 | $C_2H_5OCH_2-$ | O | CH | m.p. 156.5° C. |
| 19 | $i-C_3H_7$ | O | N | m.p. 204–206° C. |
| 20 | $i-C_3H_7$ | O | CH | m.p. 147.5–148.5° C. |

TABLE 2-continued

| Compound No. | R | Y | X | Physical property |
|---|---|---|---|---|
| 21 | $sec-C_4H_9$ | O | N | m.p. 213–213.5° C. |

The urea compound (II) as the starting compound in the process of this invention may be produced by reacting the iso(thio)cyanate compound (III) with the azinoic ester (IV) in an inert solvent.

The reaction is usually carried out at a temperature of 10° to 100° C. for a period of 1 to 48 hours. In the reaction, the azinoic ester (IV) may be used in an amount of 1 to 1.1 equivalents to 1 equivalent of the iso(thio)cyanate compound (III). As the solvent, there may be employed aromatic hydrocarbons (e.g. toluene, benzene), halogenated hydrocarbons (e.g. chloroform), ethers (e.g. dioxane, dimethoxyethane), etc. The reaction can proceed in the absence of a base. If desired, however, a catalytic amount of the base may be present in the reaction system for acceleration of the reaction. Examples of such base are organic bases (e.g. triethylamine, N,N-diethylaniline).

The reaction mixture is, after completion of the reaction, subjected to an ordinary post-treatment such as dilution with water, extraction with an organic solvent and concentration. If necessary, any conventional purification procedure such as chromatography or recrystallization may be applied.

Typical examples for production of the pyridazine compounds (II) are illustratively shown in the following Examples.

EXAMPLE 4

6-Fluoro-3-(2-propenyl)-2(3H)-benzothiazolon-5-yl isocyanate (1.99 g) and ethyl hexahydropyridazine-1-carboxylate (1.26 g) were added to toluene (8 ml). A catalytic amount of triethylamine was added thereto, and the resultant mixture was stirred at 25° C. for 12 hours. Water was added thereto, and the resultant mixture was extracted with toluene. The extract was washed with water, dried and concentrated to give ethyl 2-[6-fluoro-3-(2-propenyl)-2(3H)-benzothiazolon-5-ylaminocarbonyl]-hexahydropyridazine-1-carboxylate (2.26 g). m.p., 161.2° C.

EXAMPLE 5

6-Fluoro-3-(2-propenyl)-2(3H)-benzothiazolon-5-yl isothiocyanate (3.1 g) and ethyl hexahydropyridazine-1-carboxylate (1.17 g) were added to toluene (15 ml). A catalytic amount of triethylamine was added thereto, and the resultant mixture was stirred at 25° C. for 12 hours. Water was added thereto, and the resultant mixture was extracted with toluene. The extract was washed with water, dried and concentrated to give ethyl 2-[6-fluoro-3-(2-propenyl)-2(3H)-benzothiazolon-5-ylaminothiocarbonyl]-hexahydropyridazine-1-carboxylate (3.3 g). m.p., 40°–42° C.

In the same manner as above, the urea compounds (II) as shown in Table 3 were obtained.

TABLE 3

(II)

| R | X | Y | Z | Physical property |
|---|---|---|---|---|
| $CH_3$ | N | O | $C_2H_5O$ | m.p. 142.0–143.0° C. |
| $C_2H_5$ | N | O | $C_2H_5O$ | m.p. 171.5–173.0° C. |
| $n-C_3H_7$ | N | O | $C_2H_5O$ | $n_D^{26.2}$ 1.5597 |
| $CH_2=CHCH_2$ | N | O | $C_2H_5O$ | m.p. 161.2° C. |
| $CH\equiv CCH_2$ | N | O | $C_2H_5O$ | m.p. 197.0–198.0° C. |
| $CH_3OCH_2$ | N | O | $C_2H_5O$ | m.p. 181.0–183.0° C. |
| $CH_3CH_2OCH_2$ | N | O | $C_2H_5O$ | $n_D^{26.2}$ 1.5565 |
| $C_2H_5$ | N | S | $C_2H_5O$ | m.p. 55.0° C. |
| $n-C_3H_7$ | N | S | $C_2H_5O$ | m.p. 116.0–117.0° C. |
| $CH_2=CHCH_2$ | N | S | $C_2H_5O$ | m.p. 40.0–42.0° C. |
| $CH\equiv CCH_2$ | N | S | $C_2H_5O$ | m.p. 38.0° C. |
| $i-C_3H_7$ | N | O | $C_2H_5O$ | m.p. 178–179° C. |
| $CH\equiv CCH_2$ | CH | O | $C_2H_5O$ | m.p. 174° C. |

The iso(thio)cyanate compound (III) also usable as the starting material can be produced according to the following reaction scheme:

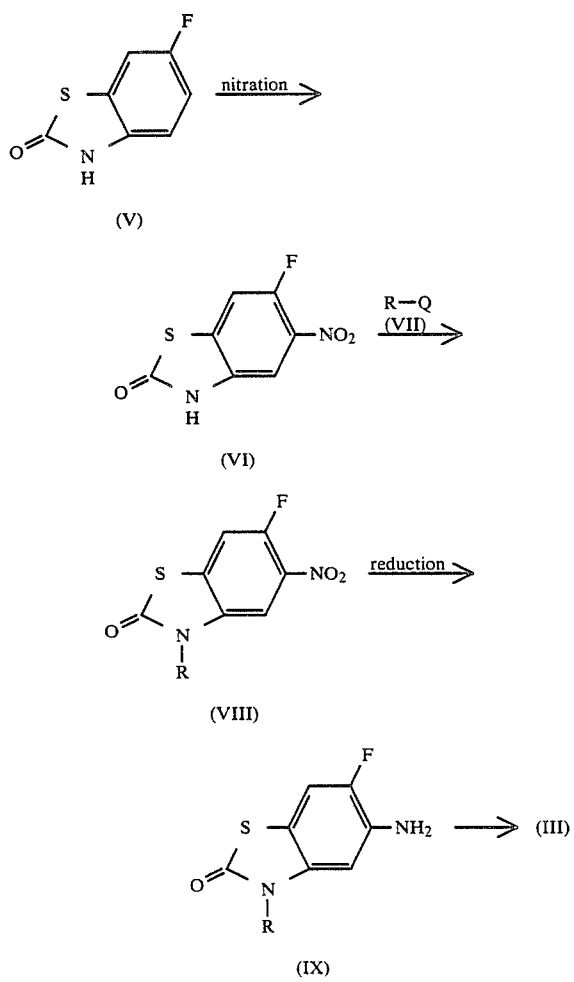

wherein R is as defined above and Q is a leaving group (e.g. chlorine, bromine, iodine, methanesulfonyloxy, p-toluenesulfonyloxy).

Explaining the above conversion, 6-fluoro-2(3H)-benzothiazolone (V) [G. Mazzone et al: Farmaco, Ed. Sc., 32, (5), 348 (1977)] is reacted with a nitrating agent such as a mixture of sulfuric acid and nitric acid to give 6-fluoro-5-nitro-2(3H)-benzothiazolone (VI). The reaction is accomplished at a temperature of −10° to 10° C. instantaneously or within 5 hours. Sulfuric acid and nitric acid are respectively used in amounts of one equivalent to excess amount and of 1 to 1.2 equivalents to the compound (V).

After completion of the reaction, the reaction mixture is poured into water, and the precipitated crystals are collected by filtration and subjected to an ordinary post-treatment such as washing with water. If necessary, any conventional purification procedure such as recrystallization or chromatography may be applied.

The thus obtained 6-fluoro-5-nitro-2(3H)-benzothiazolone (VI) is then reacted with a compound of the formula:

$$R-Q \qquad (VII)$$

wherein R and Q are each as defined above in an inert solvent in the presence of a base to give the 3-substituted-6-fluoro-5-nitro-2(3H)-benzothiazolone (VIII). The reaction proceeds at a temperature of 0° to 120° C. for a period of 30 minutes to 24 hours. The compound (VII) and the base are respectively used in amounts of 1.1 to 1.5 equivalents to one equivalent of the compound (VI). Examples of the inert solvent, of which examples are aromatic hydrocarbons (e.g. toluene, benzene), amides (e.g. N,N-dimethylformamide), sulfur compounds (e.g. dimethylsulfoxide), nitriles (e.g. acetonitrile), water, and their mixtures. As the base, there may be exemplified sodium hydride, potassium carbonate, sodium hydroxide, potassium hydroxide, etc.

The reaction mixture is, after completion of the reaction, subjected to an ordinary post-treatment such as dilution with water, extraction with an organic solvent and concentration. If necessary, any conventional purification procedure such as recrystallization and chromatography may be adopted.

The 3-substituted-6-fluoro-5-nitro-2(3H)-benzothiazolone (VIII) is then reacted with a reducing agent such as iron powder in an auxiliary solvent to give the 5-amino-3-substituted-6-fluoro-2(3H)-benzothiazolone (IX). This reaction proceeds at a temperature of 60° to 120° C. for a period of 10 minutes to 12 hours. The amount of iron powder is usually from 3 to 30 equivalents, preferably from 5 to 20 equivalents, to one equivalent of the compound (VIII). Examples of the auxiliary solvent are aqueous acetic acid, ethyl acetate, etc.

After completion of the reaction, the residue is eliminated by filtration. The filtrate is extracted with an organic solvent, and the extract is subjected to an ordinary post-treatment such as washing with water and sodium bicarbonate solution and concentration. If necessary, any conventional purification procedure such as recrystallization and chromatography may be adopted.

The 5-amino-3-substituted-6-fluoro-2(3H)-benzothiazolone (IX) is then converted into the iso(thio)cyanate compound (III) by a per se conventional manner [S. R. Sandler, W. Karo: "Organic Functional Group Preparations", Vol. 1, 364, 373, Academic Press, New York-London (1983)].

Typical examples for production of the intermediates are illustratively shown in the following Examples.

EXAMPLE 6

6-Fluoro-5-nitro-2(3H)-benzothiazolone (VI)

A solution of 6-fluoro-2(3H)-benzothiazolone (47.58 g) in 100% sulfuric acid (760 ml) was cooled at 0° to 5° C., and 98% fuming nitric acid (d=1.52; 18.79 g) was dropwise added thereto, followed by stirring at the same temperatur for 60 minutes. The reaction mixture was poured into ice-water. The precipitated crystals were collected by filtration, washed with water and dried to give 6-fluoro-5-nitro-2(3H)-benzothiazolone (48.48 g) as pale brown crystals. m.p., 180°–182° C.

EXAMPLE 7

3-Substituted-6-fluoro-5-nitro-2(3H)-benzothiazolone (VIII)

A suspension of sodium hydride (60% in oil; 0.21 g) in N,N-dimethylformamide (7 ml) was cooled to 0° C., and 6-fluoro-5-nitro-2(3H)-benzothiazolone (1.00 g) was added thereto at 0° to 5° C., followed by stirring for 30 minutes. To the suspension, allyl bromide (0.62 g) was added, and the resultant mixture was gradually heated to a temperature of 50° to 60° C. and allowed to react at the same temperature for 3 hours. Water was added to the reaction mixture, which was extracted with ethyl acetate. The extract was washed with water, dried and concentrated. The residue was purified by silica gel thin layer chromatography using a mixture of ethyl acetate and toluene (1:9) as an eluent to give 3-allyl-7-fluoro-6-nitro-2(3H)-benzothiazolone (0.70 g). m.p., 112.5°–113.5° C.

In the same manner as above, the 3-substituted-6-fluoro-5-nitro-2(3H)-benzothiazolones (XIII) as shown in Table 4 obtainable.

TABLE 4

(VIII)

| R | Physical property |
|---|---|
| $CH_3$ | m.p. 148–149° C. |
| $C_2H_5$ | m.p. 128–128.5° C. |
| $n-C_3H_7$ | m.p. 71–73° C. |
| $i-C_3H_7$ | m.p. 153–153.5° C. |
| $CH_2=CHCH_2$ | m.p. 112.5–113.5° C. |
| $CH\equiv CCH_2$ | m.p. 123.5–124.5° C. |
| $CH_3OCH_2$ | m.p. 125–126° C. |
| $C_2H_5OCH_2$ | m.p. 114–115° C. |

EXAMPLE 8

5-Amino-3-substituted-6-fluoro-2(3H)-benzothiazolone (IX)

A suspension of iron powder (0.77 g) in 5% aqueous acetic acid (1.5 ml) was heated at 80° C., and a solution of 3-allyl-6-fluoro-5-nitro-2(3H)-benzothiazolone (0.70 g) in acetic acid (2.8 ml) and ethyl acetate (2.8 ml) was added thereto, followed by heating under reflux at 60° to 80° C. for 3 hours. After cooling, water and ethyl acetate were added to the resultant mixture, followed by filtration. The filtrate was extracted with ethyl acetate, and the extract was washed with water and sodium bicarbonate solution, dried and concentrated to give 5-amino-3-allyl-6-fluoro-2(3H)-benzothiazolone (0.60 g). $n_D^{26.0}$ 1.6236.

In the same manner as above, the 5-amino-3-substituted-6-fluoro-2(3H)-benzothiazolones (IX) as shown in Table 5 were produced.

TABLE 5

(IX)

| R | Physical property |
|---|---|
| $CH_3$ | m.p. 188–189° C. |
| $C_2H_5$ | m.p. 117–119° C. |
| $n-C_3H_7$ | $n_D^{25.3}$ 1.6000 |
| $i-C_3H_7$ | $n_D^{24.4}$ 1.6056 |
| $CH_2=CHCH_2$ | $n_D^{26.0}$ 1.6236 |
| $CH\equiv CCH_2$ | m.p. 124–126° C. |
| $CH_3OCH_2$ | m.p. 112–113° C. |
| $C_2H_5OCH_2$ | m.p. 77–78° C. |

EXAMPLE 9

Iso(thio)cyanate compond (III)

A solution of 5-amino-3-isopropyl-6-fluoro-2(3H)-benzothiazolone (5 g) in toluene (70 ml) was added to 1M phosgene/toluene, and the resultant solution was stirred at 90° to 95° C. for 1 hour, followed by concentration under reduced pressure. The residue was crystallized from n-hexane to give 6-fluoro-3-isopropyl-2(3H)-benzothiazolon-5-yl isocyanate (5.2 g). m.p., 149°–150° C.

IR $\nu$ max (liquid paraffin): 2250 (=C=N=O), 1680

$(cm^{-1})$.

In the same manner as above, the iso(thio)cyanate compound (III) as shown in Table 6 were produced.

TABLE 6

(III)

| R | Y | Physical property |
|---|---|---|
| $-CH_2C\equiv CH$ | O | m.p. 117–121° C. |
| $-CH_2C\equiv CH$ | S | m.p. 125–126° C. (IR $\nu_{max}$: 2050 $(cm^{-1})$) |
| $-CH_2CH=CH_2$ | O | m.p. 101–102° C. |
| $-CH_2CH=CH_2$ | S | m.p. 92–93.5° C. (IR $\nu_{max}$: 2020, 1670 $(cm^{-1})$) |

In the practical use of the benzothiazolylazolidines (I), they may be applied in conventional preparation forms such as emulsifiable concentrates, wettable powders, suspensions and granules in combination with conventional solid or liquid carriers or diluents as well as surface active agents or auxiliary agents. The content of the benzothiazolylazolidines (I) as the active ingredient in such preparation forms is usually within a range of 0.05 to 90% by weight, preferably of 0.1 to 80% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the present invention are illustratively shown in the following examples wherein parts are by weight. The compound number of the active ingredient corresponds to the one in Table 2.

FORMULATION EXAMPLE 1

Fifty parts of Compound No. 2, 12 or 14, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Five parts of Compound No. 3, 13 or 17, 14 parts of polyoxyethylenestyrylphenyl ether, 6 parts of calcium dodecylbenzenesulfonate, 30 parts of xylene and 45 parts of cyclohexanone are well mixed to obtain an emulsifiable concentrate.

FORMULATION EXAMPLE 3

Two parts of Compound No. 8, 10, 15 or 16, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of Compound No. 5, 6 or 18 is mixed with 3 parts of polyoxyethylene sorbitan monooleate, 3 parts of carboxymethyl cellulose and 69 parts of water and pulverized until the particle size of the mixture becomes less than 5 microns to obtain a suspension.

FORMULATION EXAMPLE 5

Five parts of Compound No. 7, 9, 11, 16 or 18, 14 parts of polyoxyethylenestyrylphenyl ether, 6 parts of calcium dodecylbenzenesulfonate, 30 parts of xylene and 45 parts of N,N-dimethylformamide are mixed well to obtain an emulsifiable concentrate.

The benzothiazolylazolidines (I) thus formulated in any suitable formulation form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the benzothiazolylazolidines (I) over the top of the plants. It may also be applied directly to the weeds if care is taken to keep the chemical off the crop foliage.

The benzothiazolylazolidines (I) of the present invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Furthermore, the benzothiazolylazolidines (I) can be used as herbicides applicable to agricultural plowed fields as well as paddy fields. They are also useful as herbicides to be employed to orchards, pasture lands, lawns, forests, non-agricultural fields, etc.

The dosage rate of the benzothiazolylazolidines (I) may vary on prevailing weather conditions, formulation used, prevailing season, mode of application, soil involved, crop and weed species, etc. Generally, however, the dosage rate is from 0.02 to 100 grams, preferably from 0.05 to 50 grams, of the active ingredient per are. The herbicidal composition of the present invention formulated in the form of an emulsifiable concentrate, a wettable powder or a suspension may ordinarily be employed by diluting it with water at a volume of 1 to 10 liters per are, if necessary, with the addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the benzothiazolylazolidines (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates that no material difference is seen in comparison with the untreated plant and the numeral "5" indicates the complete inhibition or death of the test plants.

The compounds shown in Table 7 below were used for comparison.

TABLE 7

| Compound No. | Chemical structure | Remarks |
|---|---|---|
| A | 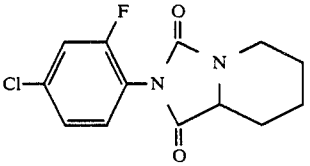 | U.S. Pat. No. 3,958,976 |

TABLE 7-continued

| Compound No. | Chemical structure | Remarks |
|---|---|---|
| B | (benzothiazolinone structure with S, O=, N-CH₂CO₂H, Cl) | Commercially available herbicide "benazolin" |

TEST EXAMPLE 1

Cylindrical plastic pots (diameter, 10 cm; height, 10 cm) were filled with upland field soil, and the seeds of Japanese millet, oats, tall morningglory and velvetleaf were sowed therein and covered with soil. A designated amount of the test compound formulated in an emulsifiable concentrate according to Formulation Example 2 or 5 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 8.

TABLE 8

| Compound No. | Dosage (g/are) | Japanese millet | Oats | Tall morningglory | Velvetleaf |
|---|---|---|---|---|---|
| 1 | 20 | 5 | — | 5 | 5 |
| 2 | 20 | 5 | — | 5 | 5 |
|   | 5 | 5 | — | 5 | 5 |
| 3 | 20 | 5 | — | 5 | 5 |
|   | 5 | 5 | — | 5 | 5 |
| 4 | 20 | 5 | — | 5 | 5 |
|   | 5 | 5 | — | 5 | 5 |
| 5 | 20 | 5 | — | 5 | 5 |
| 6 | 20 | 5 | — | 5 | 5 |
| 7 | 20 | 5 | — | 5 | 5 |
| 8 | 20 | 5 | — | 5 | 5 |
| 9 | 20 | 5 | — | 5 | 5 |
| 10 | 20 | 5 | — | 5 | 5 |
|   | 5 | 5 | — | 5 | 5 |
| 11 | 20 | 5 | — | 5 | 5 |
| 12 | 20 | 5 | 5 | 5 | 5 |
| 13 | 20 | 5 | 5 | 5 | 5 |
| 14 | 20 | 5 | 5 | 5 | 5 |
| 15 | 20 | 5 | 5 | 5 | 5 |
| 16 | 20 | 5 | 5 | 5 | 5 |
| 17 | 20 | 5 | 5 | 5 | 5 |
| 18 | 20 | 5 | 5 | 5 | 5 |
| B | 20 | 2 | — | 3 | 4 |
|   | 5 | 0 | — | 0 | 1 |

TEST EXAMPLE 2

Cylindrical plastic pots (diameter, 10 cm, height, 10 cm) were filled with upland field soil, and the seeds of Japanese millet, oats, radish and velvetleaf were sowed therein and cultivated in a greenhouse for 10 days. A designated amount of the test compound formulated in an emulsifiable concentrate according to Formulation Example 2 or 5 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined The results are shown in Table 9.

TABLE 9

| Compound No. | Dosage (g/are) | Japanese millet | Oats | Radish | Velvetleaf |
|---|---|---|---|---|---|
| 2 | 20 | 5 | 5 | — | — |
| 4 | 20 | 5 | 5 | — | — |
| 6 | 20 | 5 | 5 | — | — |
| 8 | 20 | 5 | 5 | — | — |
| 10 | 20 | 5 | 5 | — | — |
| 12 | 20 | 5 | 5 | 5 | 5 |
| 13 | 20 | 5 | 5 | 5 | 5 |
| 14 | 20 | 5 | 5 | 5 | 5 |
| 15 | 20 | 5 | 5 | 5 | 5 |
| 16 | 20 | 5 | 5 | 5 | 5 |
| 17 | 20 | 5 | 5 | 5 | 5 |
| 18 | 20 | 5 | 5 | 5 | 5 |
| B | 20 | 0 | 0 | — | — |

TEST EXAMPLE 3

Cylindrical plastic pots (diameter, 8 cm,; height, 12 cm) were filled with paddy field soil, and the seeds of barnyardgrass (*Echinochloa oryzicola*), broad-leaved weeds (i.e. common falsepimpernel, indian toothcup, waterwort) were sowed in 1 to 2 cm depth. Water was poured therein to make a flooded condition. Buds of arrowhead were sowed in 1 to 2 cm depth, and rice seedlings of the 2.5-leaf stage were transplanted therein, and the test plants were grown in a greenhouse. Six days (at that time weeds began to germinate) thereafter, a designated amount of the test compound formulated in an emulsifiable concentrate according to Formulation Example 2 or 5 and diluted with water (5 ml) was applied to the pots by perfusion. The test plants were grown for an additional 20 days in the greenhouse, and the herbicidal activity was examined. The results are shown in Table Table 10.

TABLE 10

| Compound No. | Dosage (g/are) | Barnyardgrass | Broadleaved weed | Arrowhead |
|---|---|---|---|---|
| 2 | 0.63 | 5 | 5 | 5 |
| 4 | 0.63 | 5 | 5 | 5 |
| 13 | 0.63 | 5 | 5 | 5 |
| 14 | 0.63 | 5 | 5 | 5 |
| 15 | 0.63 | 5 | 5 | 5 |
| 16 | 0.63 | 5 | 5 | 5 |
| A | 0.63 | 3 | 4 | 1 |
| B | 0.63 | 0 | 1 | 0 |

TEST EXAMPLE 4

Vats (33 cm×23 cm×11 cm) were filled with upland field soil, and the seeds of soybean, cotton, corn, rice plant, common cocklebur, velvetleaf, sicklepod, black nightshade, common lambsquarters, redroot pigweed, barnyard-grass (*Echinochloa crus-galli*), johnsongrass and green foxtail were sowed therein to 1 to 2 cm depth. A designated amount of the test compound formulated in an emulsifiable concentrate according to Formulation Example 2 or 5 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 11.

TABLE 11

| Compound No. | Dosage (g/are) | Soybean | Cotton | Corn | Rice plant | Common cocklebur | Velvetleaf | Sicklepod | Black nightshade | Redroot pigweed | Common lambsquarters | Green foxtail | Barnyardgrass | Johnsongrass |
|---|---|---|---|---|---|---|---|---|---|---|---|---|---|---|
| 2 | 1.25 | — | — | 1 | — | — | 5 | 5 | 5 | 5 | 5 | 4 | — | 5 |
| 4 | 1.25 | — | — | 0 | 1 | — | 5 | — | 4 | 5 | 5 | — | — | 4 |
| 8 | 1.25 | — | — | 1 | 1 | — | 5 | — | 4 | 5 | 5 | 4 | — | 5 |
| 10 | 1.25 | — | — | 0 | 1 | — | 5 | — | 5 | 5 | 5 | 4 | — | 4 |
| 12 | 5 | 2 | — | — | — | 5 | 5 | 5 | 5 | 5 | 5 | 4 | 4 | 4 |
|  | 2.5 | 1 | 2 | 2 | — | 4 | 4 | — | 4 | 4 | 4 | 4 | — | — |
| 13 | 5 | — | — | 2 | — | 5 | 5 | 5 | 5 | 5 | 5 | 5 | 5 | 5 |
|  | 2.5 | — | 2 | 1 | — | 5 | 5 | 5 | 4 | 5 | 5 | 5 | 5 | 5 |
| 14 | 5 | — | — | — | — | — | 5 | — | 5 | 5 | 5 | 5 | 5 | 5 |
|  | 2.5 | — | — | — | — | — | 5 | — | — | 5 | 5 | 4 | 4 | 4 |
| 15 | 5 | — | 2 | — | — | 4 | 5 | 4 | 5 | 5 | 5 | 5 | 5 | 5 |
|  | 2.5 | 2 | 1 | 1 | — | 4 | 5 | 4 | 4 | 4 | 4 | 4 | 4 | 4 |
| 16 | 5 | — | — | — | — | 5 | 5 | 5 | 5 | 5 | 5 | 5 | 5 | 5 |
|  | 2.5 | 1 | — | — | — | 5 | 5 | 5 | 5 | 5 | 5 | 5 | 4 | 5 |
| 17 | 5 | — | — | — | — | 5 | 5 | 4 | 5 | 5 | 5 | 5 | 5 | 5 |
|  | 2.5 | — | — | — | — | 4 | 5 | — | 5 | 5 | 5 | 5 | 4 | 5 |
| 18 | 5 | 1 | 1 | 2 | — | — | 5 | 5 | 5 | 5 | 5 | 4 | 4 | — |
| A | 5 | 0 | 1 | 0 | — | 2 | 3 | 2 | 4 | 5 | 5 | 2 | 2 | 2 |
|  | 2.5 | 0 | 1 | 0 | — | 0 | 2 | 0 | 3 | 3 | 3 | 1 | 1 | 1 |
| B | 5 | 0 | 0 | 0 | — | 1 | 3 | 0 | 3 | 3 | 3 | 0 | 0 | 0 |
|  | 2.5 | 0 | 0 | 0 | — | 0 | 0 | 0 | 0 | 0 | 0 | 0 | 0 | 0 |

TEST EXAMPLE 5

Vats (33 cm × 23 cm × 11 cm) were filled with upland field soil, and the seeds of wheat, catchweed bedstraw, common chickweed, persian speedwell, field pansy, wild mustard, wild oats and blackgrass were sowed in 1 to 2 cm depth. A designated amount of the test compound formulated in an emulsifiable concentrate according to Formulation Example 2 or 5 was diluted with water and the dilution was sprayed to the surface of the soil by means of a small hand sprayer at a spray volume of 10 liters per are. The test plants were grown in a greenhouse for 27 days, and the herbicidal activity was examined. The results are shown in Table 12.

TABLE 12

| Compound No. | Dosage (g/are) | Wheat | Catchweed bedstraw | Common chickweed | Persian speedwell | Field pansy | Wild mustard | Wild oats | Blackgrass |
|---|---|---|---|---|---|---|---|---|---|
| 6 | 1.25 | 1 | 4 | 5 | 5 | 5 | 5 | 4 | 4 |
| 9 | 1.25 | 1 | 5 | 5 | 5 | — | 5 | — | 4 |
| 10 | 1.25 | 1 | 4 | 5 | 5 | 5 | 5 | — | — |

TEST EXAMPLE 6

Vats (33 cm × 23 cm × 11 cm) were filled with upland field soil, and the seeds of wheat, catchweed bedstraw, common chickweed, persian speedwell, field pansy, wild oats and blackgrass were sowed in 1 to 2 cm depth. A designated amount of the test compound formulated in an emulsifiable concentrate according to Formulation Example 2 or 5 was diluted with water and the dilution was sprayed to the surface of the soil by means of a small hand sprayer at a spray volume of 10 liters per are. The test plants were grown in a greenhouse for 20 days, and the herbicidal activity was examined. The results are shown in Table 13.

TABLE 13

| Compound No. | Dosage (g/are) | Wheat | Catchweed bedstraw | Common chickweed | Persian speedwell | Field pansy | Wild oats | Blackgrass |
|---|---|---|---|---|---|---|---|---|
| 15 | 2.5 | — | 5 | 5 | 5 | 5 | 5 | 5 |
|  | 1.25 | — | 5 | 5 | 5 | 4 | 4 | 5 |
| 16 | 2.5 | — | 5 | 5 | 5 | 5 | 5 | 5 |
|  | 1.25 | 1 | — | 5 | 5 | — | 4 | 5 |
| 17 | 2.5 | 2 | — | 5 | 5 | 5 | 4 | 5 |
|  | 1.25 | 2 | — | 5 | 5 | 5 | 4 | 5 |
| A | 2.5 | 1 | 1 | 2 | 4 | 3 | 0 | 1 |
|  | 1.25 | 0 | 0 | 1 | 2 | 2 | 0 | 0 |

TEST EXAMPLE 7

Vats (33 cm × 23 cm × 11 cm) were filled with upland field soil, and the seeds of corn, rice plant, tall morningglory, velvetleaf, black nightshade, redroot pigweed and common lambsquarters were sowed therein and cultivated for 18 days in a greenhouse. A designated amount of the test compound formulated in an emulsifiable concentrate according to Formulation Example 2 or 5 was diluted with water containing a spreading agent, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although growing stage of the test plants varied depending on their species. The results are shown in Table 14.

TABLE 14

| Compound No. | Dosage (g/are) | Herbicidal activity | | | | | | |
| --- | --- | --- | --- | --- | --- | --- | --- | --- |
| | | Corn | Rice plant | Tall morning-glory | Velvet-leaf | Black night-shade | Redroot pigweed | Common lambs-quarters |
| 2 | 0.1 | 0 | — | — | 4 | 4 | 4 | — |
| 3 | 0.1 | 1 | 1 | 4 | 4 | 5 | 4 | — |
| 9 | 0.1 | 1 | 1 | 4 | 4 | 5 | 4 | — |
| 10 | 0.1 | 1 | 0 | 4 | 5 | 5 | 5 | — |
| 13 | 0.1 | 1 | — | 5 | 5 | 5 | 5 | 5 |
| 14 | 0.1 | 1 | — | 5 | 5 | 5 | 5 | 5 |
| 15 | 0.1 | 1 | — | 5 | 5 | 5 | 5 | 5 |
| 16 | 0.1 | 1 | — | 5 | 5 | 5 | 5 | 5 |
| 17 | 0.1 | 1 | — | 5 | 5 | 5 | 5 | 5 |
| B | 0.1 | 0 | — | 0 | 0 | 0 | 0 | 0 |

TEST EXAMPLE 8

Wagner's pots (1/5000 are) were filled with paddy field soil, and the seeds of barnyardgrass (*Echinochloa oryzicola*), broad-leaved weeds (e.g. common falsepimpernel, indian toothcup, waterwort) and statoblast of needle spikerush were sowed in 1 to 2 cm depth. Water was poured therein to make a flooded condition. Rice seedlings of the 3-leaf stage were transplanted therein and grown in a greenhouse. Thirteen days (at that time barnyardgrass began to germinate) thereafter, a designated amount of the test compound formulated in an emulsifiable concentrate according to Formulation Example 2 or 5 and diluted with water (10 ml) was applied to the pots by perfusion, followed by addition of water thereto to make a 4 cm depth. The test plants were grown for an additional 20 days in the greenhouse, and the herbicidal activity was examined. Two consecutive days after the treatment, water was leaked out in an amount of 3 cm depth per day. The results are shown in Table 15.

TABLE 15

| Compound No. | Dosage (g/are) | Herbicidal activity | | | |
| --- | --- | --- | --- | --- | --- |
| | | Rice plant | Barnyard-grass | Broadleaved weed | Needle spikerush |
| 15 | 0.16 | 1 | 5 | 5 | 4 |
| 16 | 0.16 | 1 | 5 | 5 | 4 |
| A | 0.16 | 0 | 0 | 1 | 0 |

What is claimed is:

1. A compound of the formula:

wherein R is a $C_1$-$C_5$ alkyl group, a $C_3$-$C_5$ alkenyl group, a $C_3$-$C_5$ alkynyl group or a $C_1$-$C_3$ alkoxy ($C_1$-$C_3$) alkyl group, and Y is a sulfur or an oxygen atom.

2. The compound according to claim 1, wherein Y is an oxygen atom.

3. The compound according to claim 1, wherein R is a $C_2$-$C_4$ alkyl group, a $C_3$-$C_4$ alkenyl group, a $C_3$-$C_4$ alkynyl group or a $C_1$-$C_3$ alkoxymethyl group.

4. The compound according to claim 1, wherein R is an ethyl group, an isopropyl group, an allyl group, a propargyl group, a 1-methyl-2-propynyl group or a methoxy-methyl group.

5. The compound according to claim 2, wherein R is an ethyl group, an isopropyl group, an allyl group, a propargyl group, a 1-methyl-2-propynyl group or a methoxy-methyl group.

6. The compound according to claim 1, which is 2-[3-(2-propynyl)-6-fluoro-2(3H)-benzothiazolon-5-yl]-4,5,6,7-tetrahydro-1H-[1,2,4]triazolo [1,2-a]pyridazine-1,3(2H)-dione.

7. The compound according to claim 1, which is 2-[3-(2-propynyl)-6-fluoro-2(3H)-benzothiazolon-5-yl]-hexahydro-1-thioxo-1H-[1,2,4]triazolo[1,2-a]pyridazin-3-one.

8. A herbicidal composition which comprises as an essential active ingredient a herbicidally effective amount of the compound of claim 1 and an inert carrier or diluent.

9. A method for controlling undesired weeds, which comprises applying a herbicidally effective amount of the compound according to claim 1 and an inert carrier or diluent to the area where undesired weeds grow or will grow.

* * * * *